(12) United States Patent
Kalota

(10) Patent No.: US 8,232,398 B2
(45) Date of Patent: *Jul. 31, 2012

(54) RECYCLING PROCESS FOR INCREASING THE YIELD OF OPIATE ALKALOID DERIVATIVES

(75) Inventor: Dennis J. Kalota, Fenton, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 459 days.

This patent is subject to a terminal disclaimer.

(21) Appl. No.: 12/586,856

(22) Filed: Sep. 29, 2009

(65) Prior Publication Data

US 2010/0081815 A1  Apr. 1, 2010

Related U.S. Application Data

(60) Provisional application No. 61/194,697, filed on Sep. 30, 2008.

(51) Int. Cl.
*C07D 489/12* (2006.01)
*C07D 489/10* (2006.01)

(52) U.S. Cl. ............................................ 546/39; 546/38

(58) Field of Classification Search .................... 546/39, 546/38

See application file for complete search history.

(56) References Cited

U.S. PATENT DOCUMENTS

| | | | |
|---|---|---|---|
| 3,433,791 | A | 3/1969 | Bentley |
| 3,905,981 | A | 9/1975 | Olofson et al. |
| 4,613,668 | A | 9/1986 | Rice |
| 5,849,915 | A | 12/1998 | Kim et al. |
| 6,291,675 | B1 | 9/2001 | Coop et al. |
| 6,395,900 | B1 | 5/2002 | Coop et al. |
| 2002/0045755 | A1 | 4/2002 | Coop et al. |
| 2004/0077863 | A1 | 4/2004 | Scammells et al. |
| 2005/0164358 | A1 | 7/2005 | Carnell et al. |

FOREIGN PATENT DOCUMENTS

| | | |
|---|---|---|
| EP | 1 439 179 A1 | 7/2004 |
| WO | WO 2007/081506 | 7/2007 |

OTHER PUBLICATIONS

Breeden et al., "6-0-Demethylation of the Thevinols . . .", Helvetica Chimica Acta, 1999, 82(11), pp. 1978-1980.

*Primary Examiner* — Charanjit Aulakh

(57) ABSTRACT

The present invention provides processes for the production of opiate alkaloids. In particular, the present invention provides processes for increasing the yield of opiate alkaloids by introducing at least one recycling step.

20 Claims, No Drawings

RECYCLING PROCESS FOR INCREASING THE YIELD OF OPIATE ALKALOID DERIVATIVES

CROSS REFERENCE TO RELATED APPLICATIONS

This application claims priority from U.S. Provisional Application No. 61/194,697, filed on Sep. 30, 2008, which is hereby incorporated by reference in its entirety.

FIELD OF THE INVENTION

The present invention generally relates to processes for synthesis of opiate alkaloids. In particular, the present invention provides processes for increasing the yield of opiate alkaloids by introducing at least one recycling step.

BACKGROUND OF THE INVENTION

Thebaine is an opiate alkaloid. While thebaine is not used therapeutically itself, it can be converted industrially into a variety of therapeutically important opiate alkaloids including oxycodone, oxymorphone, nalbuphine, naloxone, naltrexone, diprenorphine, buprenorphine and etorphine. Buprenorphine, for example, is a thebaine derivative with powerful analgesia approximately twenty-five to forty times as potent as morphine, and is indicated for the treatment of moderate to severe chronic pain or for pre-operative analgesia. Buprenorphine is also used to treat opiate addiction.

Buprenorphine is generally made via a synthetic route that starts with thebaine or oripavine undergoing a cycloaddition reaction, which is then followed by a hydrogenation reaction. The resultant ketone, 1-[(5α,7α)-4,5-epoxy-18,19-dihydro-3,6-dimethoxy-17-methyl-6,14-ethenomorphinan-7-yl]-ethanone, undergoes an addition reaction in which a tertiary butyl group is added to the C7 acetyl group to produce α-(1,1-dimethylethyl)-4,5-epoxy-18,19-dihydro-3,6-dimethoxy-α,17-dimethyl-6,14-ethenomorphinan-7-methanol. This addition reaction is inefficient because some of the product that is formed is converted back to the starting material, which is then discarded during the subsequence work up procedure. Since this addition reaction is an early step in the synthesis of buprenorphine and the yield of this step is low, it contributes significantly to the low overall yield of the buprenorphine synthesis process. A need therefore exists for a process that increases the yield of this addition step in the synthesis of buprenorphine and related opiate alkaloids.

SUMMARY OF THE INVENTION

The present invention provides a process for increasing the yield of the addition reaction product. In particular, the process comprises recycling a filtrate produced during the isolation of the addition reaction product that comprises unreacted starting material. The filtrate is recycled by combining it with a subsequent addition reaction mixture.

Accordingly, one aspect of the invention provides for a process for the preparation of a compound comprising Formula (II). The process comprises forming a reaction mixture comprising a compound comprising Formula (I) and $R^9MgX^1$ such that a reaction occurs to yield a reaction product comprising the compound comprising Formula (II) and an amount of the compound comprising Formula (I) that is unreacted. The process further comprises quenching the reaction product and filtering the quenched reaction product to form a filtrate comprising an amount of the compound comprising Formula (I) and an amount of the compound comprising Formula (II). The process further comprises recycling the filtrate by combining it with a new reaction mixture and repeating the steps of the process. The following scheme depicts the reaction:

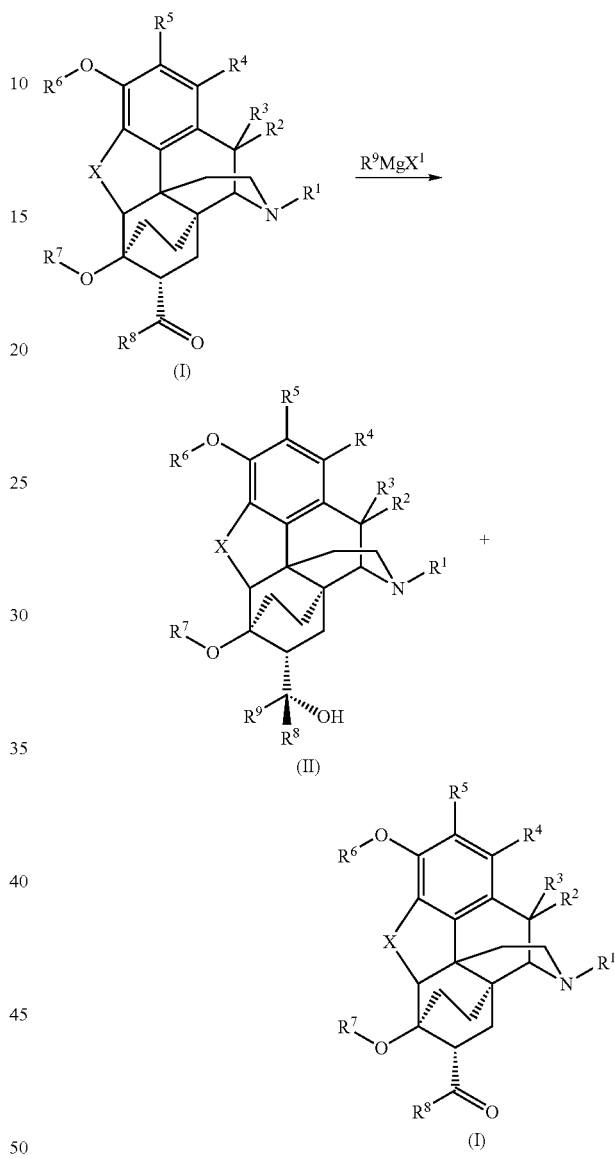

wherein:
$R^1$, $R^8$, $R^9$, and $R^{10}$ are independently selected from the group consisting of hydrocarbyl and substituted hydrocarbyl;
$R^2$ and $R^3$ are independently selected from the group consisting of hydrogen, hydrocarbyl and substituted hydrocarbyl;
$R^4$ and $R^5$ are independently selected from the group consisting of hydrogen, hydrocarbyl, substituted hydrocarbyl, halogen, {—}OH, {—}NH$_2$, {—}SH, {—}SR$^{10}$, and {—}OR$^{10}$;
$R^6$ and $R^7$ are independently selected from the group consisting of hydrogen, a protecting group, hydrocarbyl, and substituted hydrocarbyl;
X is a heteroatom; and
$X^1$ is a halogen atom.

Another aspect of the invention encompasses a process for the preparation of a compound comprising Formula (IIa). The process comprises forming a reaction mixture that comprises a compound comprising Formula (IIa) and tertiary-butylMgX$^1$, wherein X$^1$ is a halogen atom. In the reaction mixture a reaction occurs to yield a reaction product that comprises the compound comprising Formula (IIa) and an amount of the compound comprising Formula (Ia) that is unreacted. The process further comprises quenching the reaction product and filtering the quenched reaction product to form a filtrate comprising an amount of the compound comprising Formula (Ia) and an amount of the compound comprising Formula (IIa). The process further comprises recycling the filtrate by combining it with a new reaction mixture and repeating the steps of the process. The reaction of this process is depicted in the following reaction scheme:

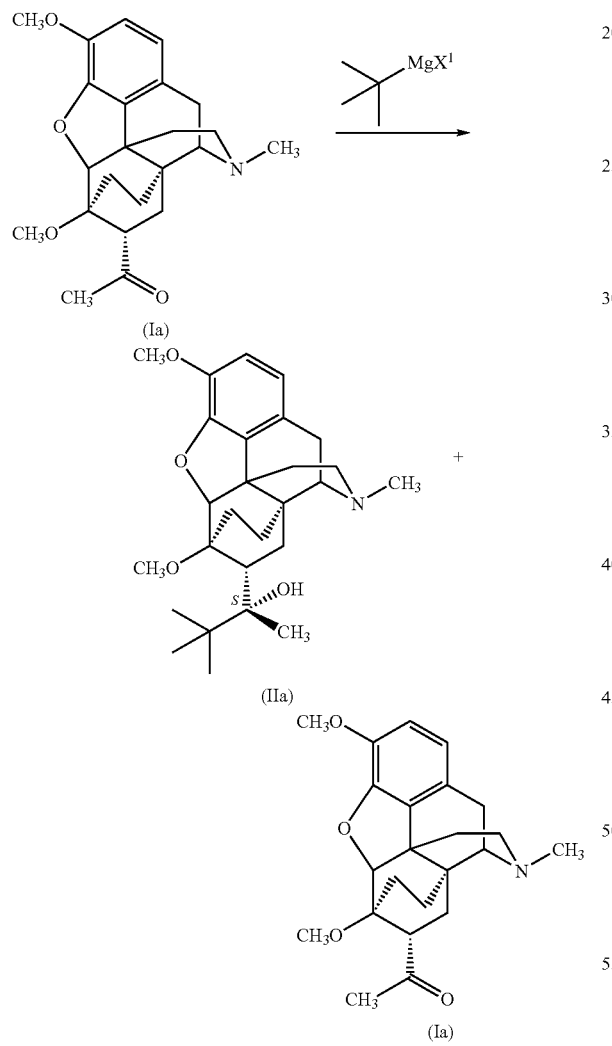

Additional aspects and iterations of the invention are described in more detail below.

DETAILED DESCRIPTION

The present invention provides processes for increasing the yield of opiate alkaloids. In particular, the process comprises recycling the unreacted ketone from the addition reaction to subsequent addition reactions, Isolation of the addition reaction product by filtration produces a filtrate comprising small amounts of the addition reaction product and the unreacted ketone. It has been discovered, and demonstrated in the examples, that recycling the filtrate by combining it with a subsequent addition reaction mixture comprising virgin ketone increases the yield of the addition product by at least 20% compared to when no recycling step is performed, based on virgin ketone charged.

Provided herein, therefore, is a recycling process for increasing the yield of a compound comprising Formula (II) during the synthesis of opiate alkaloids. The process comprises forming a reaction mixture comprising a compound comprising Formula (I) and a magnesium halide reagent (i.e., R$^9$MgX$^1$). A reaction occurs in the reaction mixture to yield a reaction product comprising the compound comprising Formula (II) and an amount of the compound comprising Formula (I) that is unreacted. The reaction that produces the compound comprising Formula (II) is generally known as a Grignard reaction. The process further comprises quenching the reaction product and filtering the reaction product to form a filtrate comprising an amount of the compound comprising Formula (I) and an amount of the compound comprising Formula (II). The process further comprises recycling the filtrate by combining the filtrate with a new reaction mixture and repeating the process, such that the yield of the compound comprising Formula (II) is increased. For the purposes of illustration, the following reaction scheme depicts the production of the compound comprising Formula (II) in accordance with an aspect of the invention:

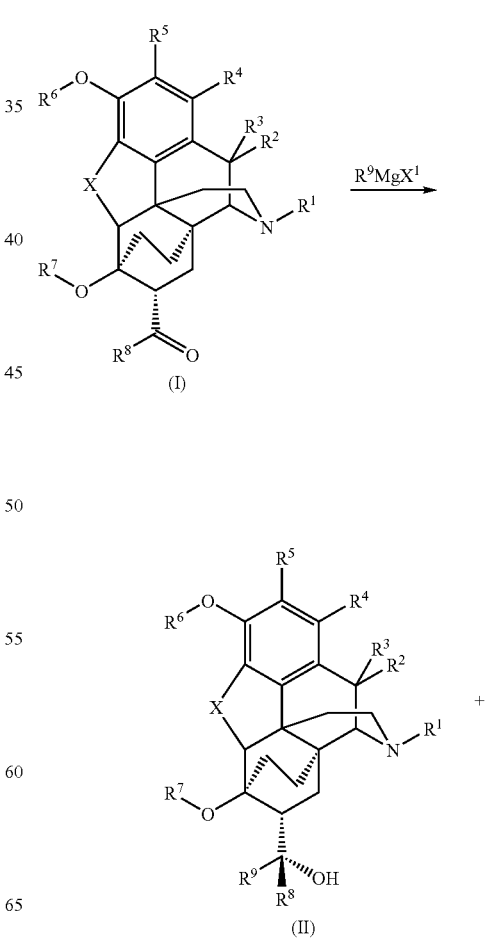

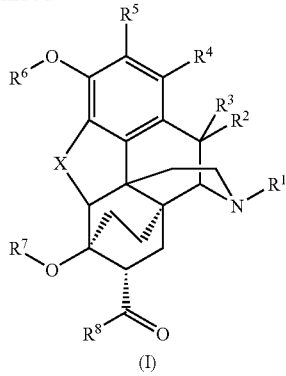

(I)

wherein:
  $R^1$, $R^8$, $R^9$, and $R^{10}$ are independently selected from the group consisting of hydrocarbyl and substituted hydrocarbyl;
  $R^2$ and $R^3$ are independently selected from the group consisting of hydrogen, hydrocarbyl and substituted hydrocarbyl;
  $R^4$ and $R^5$ are independently selected from the group consisting of hydrogen, hydrocarbyl, substituted hydrocarbyl, halogen, {—}OH, {—}$NH_2$, {—}SH, and {—}$OR^{10}$;
  $R^6$ and $R^7$ are independently selected from the group consisting of hydrogen, a protecting group, hydrocarbyl, and substituted hydrocarbyl;
  X is a heteroatom; and
  $X^1$ is a halogen atom.

In one embodiment of the process, $R^1$, $R^6$, $R^7$, and $R^8$ are alkyl or substituted alkyl, $R^9$ is an alkyl, aryl, substituted alkyl, or substituted aryl, and X is oxygen. In an iteration of this embodiment, $R^2$, $R^3$, $R^4$, and $R^5$ are hydrogen. In another embodiment, $R^2$, $R^3$, $R^4$, and $R^5$ are hydrogen. In an iteration of this embodiment, X is oxygen. In yet another embodiment, $R^1$, $R^6$, $R^7$, and $R^8$ are methyl. In an iteration of this embodiment, X is oxygen. In a further iteration of this embodiment, $R^9$ is tertiary butyl. In still another embodiment, $R^9$ is an alkyl or substituted alkyl, and Xi is chloride or bromide.

In an exemplary embodiment, the compound comprising Formula Op is the compound comprising Formula (IIa):

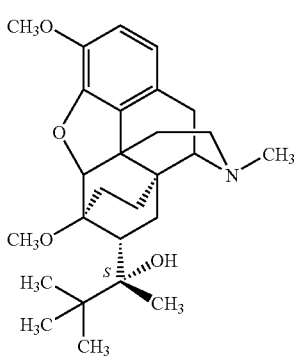

(IIa)

(a) Reaction Mixture

The process commences with formation of a reaction mixture by combining a compound comprising Formula (I) with a reagent comprising a magnesium halide in a solvent system comprising an aprotic solvent. A variety of compound comprising Formula (I) are suitable for use in this invention. In one embodiment of the process, for the compound comprising Formula (I), $R^1$, $R^6$, $R^7$, and $R^8$ are alkyl or substituted alkyl, and X is oxygen. In an iteration of this embodiment, $R^2$, $R^3$, $R^4$, and $R^5$ are hydrogen. In another embodiment, $R^2$, $R^3$, $R^4$, and $R^5$ are hydrogen. In an iteration of this embodiment, X is oxygen. In yet another embodiment, $R^1$, $R^6$, $R^7$, and $R^8$ are methyl. In an iteration of this embodiment, X is oxygen.

In one exemplary embodiment of the process, the compound comprising Formula (I) is the compound comprising Formula (Ia):

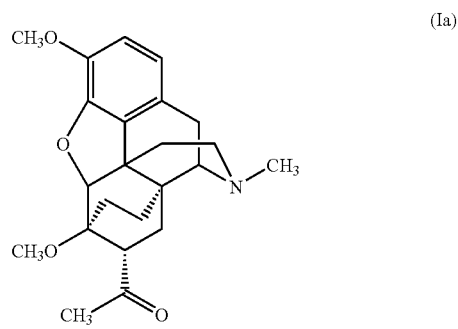

(Ia)

The reaction mixture also includes a magnesium halide reagent (i.e., $R^9MgX^1$). Such reagents are also known as Grignard reagents. In general, $R^9$ is a hydrocarbyl or a substituted hydrocarbyl, and $X^1$ is a halogen. Preferably, $X^1$ may be chloride or bromide. In one embodiment, $R^9$ may be an alkyl, aryl, substituted alkyl, or substituted aryl. In a preferred embodiment, $R^9$ may be an alkyl or substituted alkyl. The alkyl or substituted alkyl may have about 12 carbons or less, or more preferably, about 6 carbons or less. Preferred $R^9$ groups include methyl, ethyl, n-propyl, n-butyl, f-butyl, n-amyl, cyclohexyl, and the like. In a preferred embodiment, $R^9$ may be tertiary butyl. In an exemplary embodiment, the Grignard reagent may be tertiary-butyl magnesium chloride. The molar ratio of the compound comprising Formula (I) or (Ia) to the Grignard reagent can and will vary. Typically, the molar ratio of the compound comprising Formula (I) or (Ia) to the Grignard reagent may range from about 1:1 to about 1:5. In some embodiments, the molar ratio of the compound comprising Formula (I) or (Ia) to the Grignard reagent may be 1:1.0, 1:1.5, 1:2.0, 1:2.5, 1:3.0, 1:3.5, 1:4.0, 1:4.5, or 1:5.0. In a preferred embodiment, the molar ratio of the compound comprising Formula (I) or (Ia) to the Grignard reagent may range from about 1:2.5 to about 1:3.5.

The reaction mixture, as detailed herein, also includes a solvent system comprising an aprotic solvent. A variety of aprotic solvents are suitable for use in the reaction of the process of the invention. Non-limiting examples of suitable aprotic solvents include diethoxymethane, diethyl ether, dimethyl sulfoxide (DMSO), 1,2-dimethoxyethane (DME), dimethoxymethane, bis(2-methoxyethyl)ether, hexamethylphosphoramide, methylene chloride, nitrobenzene, nitromethane, sulfolane, tetrahydrofuran (THF), 2-methyl tetrahydrofuran, and combinations thereof. Preferably, the aprotic solvent may be diethyl ether or tetrahydrofuran. In general, the solvent system may also comprise an organic solvent. Suitable organic solvents include, but are not limited to, benzene, t-butyl methylether, chlorobenzene, chloromethane, cyclohexane, dichloromethane, dichloroethane, diethyl ether, fluorobenzene, heptane, hexane, toluene, and combinations thereof. Preferably, the organic solvent may be toluene or heptane. Preferably, the organic solvent may be toluene or heptane. In one exemplary embodiment, therefore, the solvent system may comprise tetrahydrofuran and toluene. In another exemplary embodiment, the solvent system may comprise toluene, heptane, and tetrahydrofuran. The weight ratio of the solvent system to the compound comprising Formula (I) or (Ia) may vary. In general, the weight ratio of the solvent system to the compound comprising Formula (I) or (Ia) may range from about 3:1 to about 30:1. In a preferred embodiment, the weight ratio of the solvent system to the compound comprising Formula (I) or (Ia) may range from about 7:1 to about 15:1. In some preferred embodiments, the weight ratio of the solvent system to the compound comprising Formula (I) or (Ia) may be about 7:1, 8:1, 9:1, 10:1, 11:1, 12:1, 13:1, 14, or 15:1.

(b) Reaction Conditions

The temperature of the reaction of the process can and will vary. In general, the reaction is conducted at a temperature that ranges from about 15° C. to about 100° C. In certain embodiments, the temperature of the reaction may be about 15°, 20°, 25°, 30°, 35°, 40°, 45°, 50°, 55°, 60°, 65°, 70°, 75°, 80°, 85°, 90°, 95°, or 100° C. The reaction is typically conducted under an inert atmosphere (i.e., nitrogen, helium, or argon). Additionally, the reaction is preferably performed under ambient pressure.

Typically, the reaction is allowed to proceed for a sufficient period of time until the reaction is complete. In this context, a "completed reaction" generally means that the reaction mixture contains a significantly diminished amount of the compound comprising Formula (I) or (Ia) and a significantly increased amount of the compound comprising Formula (II) or (IIa) compared to the amounts of each present at the beginning of the reaction. Typically, the reaction is allowed to proceed for about one to two hours, or more preferably, about 1.5 hours.

(c) Quenching and Filtering the Reaction Product

Upon completion of the reaction, a quenching agent is added to the reaction mixture to quench the reaction product and the unreacted Grignard reagent. A preferred quenching agent is aqueous ammonium chloride, although other quenching agents known to those skilled in the art may be used, including aqueous ethyl acetate, aqueous sodium chloride, or aqueous hydrochloric acid solutions. In general, the molar ratio of the compound comprising Formula (II) or (IIa) to the quenching agent may range from about 1:1 to about 1:12. In a preferred embodiment, the molar ratio of the compound comprising Formula (II) or (IIa) to the quenching agent may range from about 1:2 to about 1:7. In certain preferred embodiment, the molar ratio of the compound comprising Formula (II) or (IIa) to the quenching agent may be about 1:2, 1:2.5, 1:3, 1:3.5, 1:4, 1:4.5, 1:5. 1:5.5, 1:6, 1:6.5, or 1:7.

Typically, the compound comprising Formula (II) or (IIa) is isolated by removing most of the solvent system to form a concentrated reaction mixture, and adding an alkane to the concentrated reaction mixture to facilitate crystallization of the compound comprising Formula (II) or (IIa). The solvent system may be removed by distillation. Typically, at least about 50% of the solvent system may be removed. In one embodiment, at least about 80% of the solvent system may be removed. In a preferred embodiment, at least about 90% of the solvent system may be removed. The concentrated reaction mixture may be heated to a temperature that ranges from about 60° C. to about 120° C. before the addition of the alkane. In a preferred embodiment, the concentrated mixture may be heated to a temperature that ranges from about 80° C. to about 100° C., or more preferably from about 90°-98° C. before the addition of the alkane.

The alkane that is added to the concentrated reaction mixture may be linear, branched, or cyclic. In a preferred embodiment, the alkane may comprise from about 4 to about 20 carbons, or more preferably, from about 6 to about 12 carbons. In an exemplary embodiment, the alkane may be heptane or cyclohexane. In general, the weight ratio of the alkane to the compound comprising Formula (II) or (IIa) may range from about 3:1 to about 10:1. In a preferred embodiment, the weight ratio of the alkane to the compound comprising Formula (II) or (IIa) may range from about 4:1 to about 6:1. In some preferred embodiment, the weight ratio of the alkane to the compound comprising Formula (II) or (IIa) may be about 4.0:1. 4.5:1, 5.0:1. 5.5:1, or 6.0:1.

The concentrated reaction mixture comprising the alkane typically is allowed to cool, wherein the compound comprising Formula (II) or (IIa) crystallizes. In some embodiments, the concentrated reaction mixture comprising the alkane may be cooled to a temperature of less than about 20° C. In an exemplary embodiment, the concentrated reaction mixture comprising the alkane may be cooled to about 15° C. The cool temperature may be maintained for a period of time that ranges from about five minutes to more than about ten hours. In a preferred embodiment, the cool temperature may be maintained from about 20 minutes to about 60 minutes.

The crystallized compound comprising Formula (II) or (IIa) may be removed from the reaction mixture by filtration. Those of skill in the art are familiar with suitable filtration procedures. Filtration of the reaction mixture also forms a filtrate, which comprises an amount of the compound comprising Formula (I) or (Ia) and an amount of the compound comprising Formula (II) or (IIa). Typically, the amount of the compound comprising Formula (I) or (Ia) in the filtrate may range from about 1 wt % to about 6 wt %, or more preferably about 3 wt %, and the amount of the compound comprising Formula (II) or (IIa) in the filtrate may range from about 2 wt % to about 10 wt %, or more preferably about 5 wt %.

(d) Recycling Step

The filtrate comprising amounts of the product and the unreacted starting material is recycled by combining it with a new reaction mixture, repeating the reaction, isolating the compound comprising Formula (II) or (IIa), and forming a filtrate, as detailed above. The recycling step may be performed one time, two times, three times, or four times. The average yield of the compound comprising Formula (II) or (IIa) increases with each recycling step. In general, the yield of the compound comprising Formula (II) or (IIa) is greater than about 70% when two recycling steps are performed. Typically, when no recycling step is performed, the yield of the compound comprising Formula (IIa) ranges from about 45% to about 55%. When four recycling steps are performed, however, the yield of the compound comprising Formula (IIa) typically increases by at least about 20% compared to when no recycling step is performed.

Additionally, the temperature range at which the compound comprising Formula (II) or (IIa) crystallizes from the concentrated reaction mixture comprising the alkane narrows and/or decreases with each recycle step. For example, in a virgin addition reaction (i.e., with no recycled filtrate) the temperature at which the compound comprising Formula (II) or (IIa) crystallizes ranges from about 15° C. to about 60° C. After four recycling steps, the temperature at which the compound comprising Formula (II) or (IIa) crystallizes ranges from about 25° C. to about 55° C. Without being bound by any particular theory, it is believed that the narrowed and lower temperature range at which the compound comprising Formula (II) or (IIa) crystallizes is due to increases in the levels of impurities.

The compound comprising Formula (II) or (IIa) prepared by the process of the present invention may be an end product itself, or it may be further derivatized in one or more steps to yield further intermediates or end products. As an example, the N-methyl group of the compound comprising Formula (IIa) may be replaced with a nitrile group to form 3-O-methyl-N-cyano-buprenorphine, which may undergo further reactions to form buprenorphine.

The compound comprising any of Formulas (I) or (II) may have a (−) or (+) optical activity with respect to the rotation of polarized light, based on whether the starting material used is in the (−) or (+) opiate absolute form. More specifically, each chiral center may have an R or an S configuration. For purposes of illustration, the ring atoms of a morphinan compound are numbered as diagrammed below:

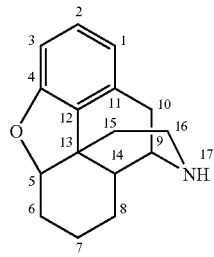

The compounds described herein may have at least six chiral centers, namely carbons C5, C6, C7, C9, C13, and C14. In general, C5 and C6 each have an R configuration, but the configuration of C7, C9, C13, and C14 may vary. The configuration of 07, C9, C13, and C14, respectively, may be RRSS, RSRR, SRSS, or SSRR, provided that the C15 and the C16 carbons are both either on the alpha face or the beta face of the molecule.

The invention also includes pharmaceutically acceptable salts of any of the compounds described herein. Exemplary salts include without limitation hydrochloride, hydrobromide, phosphate, sulfate, methansulfonate, acetate, formate, tartaric acid, maleic, malic, citrate, isocitrate, succinate, lactate, gluconate, glucuronate, pyruvate, oxalate, fumarate, propionate, aspartate, glutamate, benzoate, methyl fluoride, methyl chloride, methyl bromide, methyl iodide, and the like.

Definitions

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting an oxygen which, subsequent to the reaction for which protection is employed, may be removed without disturbing the remainder of the molecule. Exemplary protecting groups include ethers (e.g., allyl, triphenylmethyl (trityl or Tr), p-methoxybenzyl (PMS), p-methoxyphenyl (PMP)), acetals (e.g., methoxymethyl (MOM), β methoxyethoxymethyl (MEM), tetrahydropyranyl (THP), ethoxy ethyl (EE), methylthiomethyl (MTM), 2 methoxy-2-propyl (MOP), 2 trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate preferred embodiments of the invention. It should be appreciated by those of skill in the art that the techniques disclosed in the following examples represent techniques discovered by the inventors to function well in the practice of the invention. Those of skill in the art should, however, in light of the present disclosure, appreciate that many changes could be made in the specific embodiments that are disclosed and still obtain a like or similar result without departing from the spirit and scope of the invention, therefore all matter set forth is to be interpreted as illustrative and not in a limiting sense.

Example 1

Virgin Batch of Grignard Addition Reaction

A ketone charge was prepared by dissolving 87.11 g (0.2273 moles) of the ketone (i.e., compound (Ia); 1-[(5α, 7α)-4,5-epoxy-18,19-dihydro-3,6-dimethoxy-17-methyl-6,14-ethenomorphinan-7-yl]-ethanone) in 266.4 g of toluene, and the ketone solution was set aside. A 2-L jacketed flask was equipped with a mechanical stirrer, a condenser, a receiver, and an addition port sealed with a septum. After purging the flask with nitrogen, a Grignard mixture was formed by adding 614.1 g of toluene and 415.2 g of a 19.22 wt % solution of tert-butylmagnesium chloride (79.81 g, 0.6828 moles) in tetrahydrofuran (THF) to the flask. The Grignard mixture was concentrated by distilling overhead 438.5 g (42.6% of the total charge) of distillate at atmospheric pressure to a final pot oil temperature of 103° C. The composition of the Grignard solution was 79.81 g tert-BuMgCl, 142.4 g THF, and 339.7 g toluene. The concentrate in the flask was cooled to 60° C. The condenser and receiver were replaced with an addition funnel, and the ketone solution was added to the Grignard concentrate over a period of 31 minutes. The mixture was then stirred for an additional 90 minutes. The concentration of THF in the THF/toluene solvent mixture was 29.5 wt % before the ketone solution was added and 19.0 wt % after the ketone solution was added.

Upon completion of the reaction period, the mixture was cooled to 6° C. Then 367.7 g of a 20.26 wt % solution of $NH_4Cl$ (1.392 moles) in water was added over a period of 33 minutes. Then 439.4 g of water was added, followed by 87.20 g of concentrated hydrochloric acid, which afforded a pH of 3.73. The mixture was vigorously stirred until all of the solids were dissolved. Then 89.68 g of concentrated ammonium hydroxide was added, which afforded a pH of 8.77. The entire mixture was vacuum filtered through Whatman Qualitative No. 1 filter paper. The mixture was transferred to a separatory funnel and the layers were separated into a 1026.1 g lower aqueous layer and an 827.5 g upper organic layer. The aqueous layer was transferred back to the 2-L flask and 120.8 g of toluene was added. The mixture was vigorously stirred for 30 minutes. The mixture was vacuum filtered and the layers were separated into a 1001.6 g lower aqueous layer and a 119.7 g upper organic layer. The two organic layers were combined in the 2-L flask and 81.44 g of water was added. The mixture was vigorously stirred for 30 minutes. The mixture was transferred to a separatory funnel and the separated into a 177.2 g lower aqueous layer and a 920.95 g upper organic layer, which contained the alkaloids.

The 2-L flask was fitted with a short path distillation head, a condenser, and a receiver immersed in ice water. The 920.95 g organic layer was transferred to the flask. The solution was concentrated by vacuum distillation at 22 inches Hg vacuum to an overhead temperature of 75° C. and a pot oil temperature of 87° C. Approximately, 760.5 g (82.5% of the charge) of distillate was collected. The distillation head was replaced with an addition funnel, which was charged with 431.4 g of heptane. The pot oil was heated to 95° C. and the heptane was added over a period of 69 minutes. The solution was cooled. The addition product (i.e., compound (IIa); α-(1,1-dimethylethyl)-4,5-epoxy-18,19-dihydro-3,6-dimethoxy-α,17-dimethyl-6,14-ethenomorphinan-7-methanol) crystallized at a temperature of 56° C. The mixture was cooled to 15° C. and held at that temperature for 1 hr. The mixture was vacuum filtered to yield 65.27 g of wet cake and 395.96 g of filtrate. The wet cake was dried in a vacuum oven (22 inches Hg vacuum) at 65° for 13.5 hr to yield 56.17 g. Further drying at 80° C. for 30 minutes afforded 55.27 g of isolated addition product. An HPLC analysis of the isolated product found 98.95 wt % of the addition product (IIa) and 2.72 wt % of the ketone (Ia). The yield of the addition product was about 55%. The filtrate contained 4.09 wt % of the addition product and 2.90 wt % of the ketone.

Example 2

Recycling the Filtrate in Subsequent Grignard Addition Reactions

A recycling process was investigated to determine whether recycling the crystallization filtrate to a new addition process would increase the overall isolated yield of the addition product (IIa). The 2-L jacketed reactor was fitted with a mechanical stirrer, a thermometer, a short path distillation setup, and a receiver. Then 395.96 g of filtrate (from Example 1) and 528.58 g of toluene were added. The solution was moderately agitated and a 22-inch Hg vacuum was applied. The solution was concentrated with distillation occurring at pot temperatures between 69° C. and 84° C. Approximately 847.71 g of distillate was collected, leaving 76.83 g of pot oil. HPLC analysis found that the concentrate contained 15.8 wt % of ketone and 29.5 wt % of addition product.

The concentrate was used in another addition reaction. For this, 234.27 g of toluene and 76.61 g of virgin ketone were added to the concentrate. The solvent exchange vessel was rinsed with toluene, which was added to this solution making a total of 377.71 g of ketone solution. HPLC analysis of this solution found 23.52 wt % of the ketone and 5.77 wt % of the addition product. Therefore, 12% of the ketone charge was from recycle and 88% was virgin ketone. The ketone solution was set aside. A 2-L jacketed reactor was set up for the Grignard solvent exchange and an inert nitrogen atmosphere was established. To the 2-L flask was added 631.11 g of toluene and 444.71 g of a 19.22 wt % solution of tert-BuMgCl in THF. The solution was concentrated by atmospheric pressure distillation to a pot oil temperature of 103° C., which afforded 517.07 g of distillate. The Grignard solution in the flask was cooled to 60° and 365.0 g of the previously prepared ketone solution was added over a period of 63 minutes. The mixture was stirred for an additional 90 minutes.

The reaction mixture was cooled to 8° C. and then quenched with 386.59 g of a 20.26 wt % solution of ammonium chloride in water. Then 473.02 g of deionized water and 92.74 g of concentrated hydrochloric acid were added, which afforded a pH of 3.92. The mixture was aggressively stirred until most of the solids were dissolved. Then 100 g of concentrated ammonium hydroxide were added, to adjust the pH of the mixture to 8.79. The mixture was vacuum filtered and the filtrate was transferred to a separatory funnel. The layers were separated into a 1107.5 g lower aqueous layer and a 775.44 g upper organic layer, which contained the product. The water layer was transferred back to the 2-L flask and 113.8 g of toluene was added. The mixture was vigorously agitated and then the layers were separated into a 199.9 g lower aqueous layer and a 98.99 g upper organic layer. The two organic layers were combined in the 2-L flask and 88.35 g of deionized water was added. The mixture was aggressively stirred for 30 minutes. The layers were separated into a 88.77 g lower aqueous layer and a 852.13 g upper organic layer.

The combined organic layer was transferred to the 2-L flask and the solution was concentrated by vacuum distillation at 22 inches Hg vacuum, at pot oil temperatures of 45-88° C., and overhead temperatures up to 78° C. Approximately 662.7 g of distillate was obtained. Solids that formed were dissolved by adding 3.77 g of toluene. The solution was heated to 95° C., and 434.1 g of heptane was added over 52 minutes. The solution was cooled to 15° C. and held at that temperature for 65 minutes. Crystallization occurred at 43° C. The mixture was vacuum filtered affording 424.43 g of filtrate and 117.24 g of wet cake. The wet cake was dried in a vacuum oven at 20 inches Hg vacuum and 80° C. for 65 hr, which afforded 71.87 g of the addition product. The assay was 94.88 wt % of the addition product and 4.52 wt % of the ketone. Analysis of the filtrate found 5.56 wt % of the addition product and 3.03 wt % of the ketone. This procedure was repeated for all recycle batches. Table 1 presents the reaction parameters for the virgin batch and four recycle runs.

TABLE 1

Grignard Reaction Parameters.

| Run | Virgin Ketone, g (moles) | Recycled Ketone, moles | Recycled Addition Product, moles | t-BuMgCl, g (moles) | t-BuMgCl/ Ketone, mole ratio | THF in Toluene, wt % | Conversion to Addition Product, %[a] | Crystal Temp (° C.) |
|---|---|---|---|---|---|---|---|---|
| Virgin Batch | 87.11 (0.2273) | | | 79.81 (0.6828) | 3.00 | 12.81 | 79.30 | 56 |
| 1st Recycle | 76.61 (0.1999) | 0.02998 | 0.03667 | 85.47 (0.7313) | 3.18 | 12.82 | 82.88 | 43 |
| 2nd Recycle | 72.33 (0.1887) | 0.04966 | 0.08625 | 88.35 (0.7559) | 3.17 | 12.82 | 67.65 | 44 |
| 3rd Recycle | 73.11 (0.1908) | 0.03490 | 0.06574 | 89.11 (0.7623) | 3.38 | 22.86 | 70.52 | 28 |
| 4th Recycle | 78.1 (0.2038) | 0.0326 | 0.05595 | 92.55 (0.7919) | 3.35 | 15.26 | 76.82 | 48 |

[a] % = 100 * (total moles addition product in reaction mixture)/((moles virgin ketone + moles recycle ketone + moles recycle addition product).

It was found that four recycle runs was optimal—the levels of by-products increased to unacceptable levels after the fourth recycle run. These data reveal that four recycles of the filtrates increased the yield of isolated addition product from 55% to greater than 72%. Stated another way, recycling the filtrates increased the absolute yield by 17% over virgin batches, and increased the yield 31% relative to virgin batches. Table 2 presents the yields and material balance from the recycle processes.

TABLE 2

Summary of Recycle Runs.

| Run | Virgin Ketone, g | Isolated Product Total, g | Isolated Product Addition Product, g | Ketone, g | Isolated Addition Product, yield %[a] | Assay, wt % | Material Balance, %[b] |
|---|---|---|---|---|---|---|---|
| Virgin Batch | 87.11 | 55.92 | 55.33 | 1.52 | 55.1 | 98.95 | 86.17 |
| 1st Recycle | 76.61 | 71.87 | 68.19 | 3.25 | 77.24 | 94.88 | 93.73 |
| 2nd Recycle | 72.33 | 68.25 | 64.00 | 3.56 | 76.78 | 93.78 | 91.68 |
| 3rd Recycle | 73.11 | 74.63 | 65.77 | 1.686 | 78.06 | 88.13 | 83.84 |
| 4th Recycle | 78.10 | 77.44 | 70.60 | 2.168 | 78.44 | 91.17 | 90.84 |
| Total | 387.26 | 348.11 | 323.89 | 12.18 | 72.58 | | 85.69 |

[a] The isolated yield is based on the amount of virgin ketone that was charged. The amounts of the alkaloids in the recycle are not included in the yield calculation. Isolated Yield, % = 100 * ((Isolated addition product grams)/441.6)/((Virgin ketone, grams)/383.2).
[b] Material balance, % = 100 * ((323.89 + 28.17)/441.60)/((12.18 + 14.18)/383.21)/(387.26/383.21)

Table 3 summarizes the reaction parameters of additional Grignard addition reactions,

TABLE 3

Reaction Parameters.

| Run | Virgin Ketone, g (moles) | Recycled Ketone, moles | Recycled Addition Product, moles | t-BuMgCl, g (moles) | t-BuMgCl/ Ketone, mole ratio | Reaction Temp, °C. | Reaction Time, hr | THF in toluene, wt % | Conversion to Addition Product, % |
|---|---|---|---|---|---|---|---|---|---|
| 4 | 23.45 (0.0612) | | | 34.99 (0.2994) | 4.89 | 100 | 1.5 | 100 | 13.40 |
| 5 | 14.28 (0.0373) | | | 13.33 (0.1140) | 3.06 | 103 | 1.0 | 26 | 57.43 |
| 6 | 14.64 (0.0382) | | | 11.17 (0.0956) | 2.50 | 97 | 1.0 | 18.7 | 65.20 |
| 7 | 11.47 (0.0299) | 0.0044 | 0.006685 | 12.30 (0.1052) | 3.06 | 93 | 1.0 | 21.6 | 74.93 |
| 8 | 14.25 (0.0372) | | | 13.21 (0.1130) | 3.04 | 95 | 1.5 | 24.2 | 72.87 |
| 9 | 14.22 (0.0371) | 0.00276 | 0.00756 | 19.27 (0.1649) | 4.14 | 95 | 2.0 | 12.5 | 66.48 |
| 10 | 14.58 (0.0381) | 0.003473 | 0.006651 | 19.79 (0.1693) | 4.08 | 93 | 1.5 | 13.8 | 67.88 |
| 11 | 14.32 (0.0374) | 0.001884 | 0.004494 | 19.97 (0.1692) | 4.31 | 96 | 1.5 | 16.14 | 72.63 |
| 12 | 14.55 (0.0380) | 0.007278 | 0.01668 | 20.50 (0.1754) | 3.88 | 95 | 1.5 | 15.97 | 76.35 |
| 13 | 13.90 (0.0363) | | | 12.69 (0.1086) | 2.99 | 95 | 1.75 | 16.00 | 69.78 |
| 14 | 13.48 (0.0352) | | | 12.03 (0.1029) | 2.92 | 85 | 2.5 | 20.00 | 70.93 |
| 15 | 13.67 (0.0357) | | | 13.52 (0.1157) | 3.24 | 50 | 1.5 | 21.43 | 71.00 |
| 16 | 30.58[1] (0.0798) | | | 27.23 (0.2330) | 2.92 | 90 | 1.0 | 17.84 | 66.90 |
| 17 | 19.13 (0.0499) | | | 17.4 (0.1489) | 2.98 | 20 | 2.0 | 100 | 9.85 |
| 18 | 14.47 (0.0378) | | | 13.40 (0.1146) | 3.04 | 15 | 1.0 | 9.48 | 62.70 |
| 19 | 14.93 (0.0390) | | | 13.63 (0.1166) | 2.99 | 50 | 2.0 | 5.82 | 63.16 |
| 20 | 14.56 (0.0380) | | | 13.49 (0.1154) | 3.04 | 50 | 2.0 | 51.4 | 44.03 |

TABLE 3-continued

Reaction Parameters.

| Run | Virgin Ketone, g (moles) | Recycled Ketone, moles | Recycled Addition Product, moles | t-BuMgCl, g (moles) | t-BuMgCl/ Ketone, mole ratio | Reaction Temp, °C. | Reaction Time, hr | THF in toluene, wt % | Conversion to Addition Product, % |
|---|---|---|---|---|---|---|---|---|---|
| 21 | 49.43 (0.1290) | | | 50.25 (0.4300) | 3.33 | 60 | 1.5 | 19.97 | 73.20 |
| 22 | 70.48 (0.1839) | | | 70.93 (0.6069) | 3.30 | 74 | 1.1 | 16.65 | 71.30 |
| 23 | 91.31 (0.2383) | | | 72.86 (0.6233) | 2.62 | 60 | 1.1 | 13.95 | 65.55 |
| 24 | 90.13 (0.2352) | | | 76.55 (0.6550) | 2.78 | 60 | 1.5 | 17.22 | 75.87 |

[1]Un-isolated ketone.

What is claimed is:

1. A process for the preparation of a compound of Formula (II), the process comprising:

(a) forming a reaction mixture that comprises a compound of Formula (I) and $R^9MgX^1$ such that a reaction occurs to yield a reaction product that comprises the compound of Formula (II) and an amount of the compound of Formula (I) that is unreacted according to the following reaction scheme:

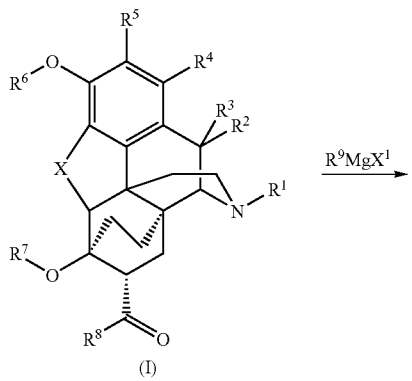

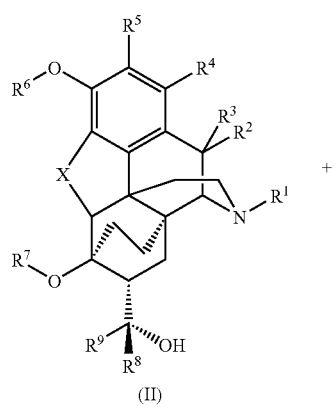

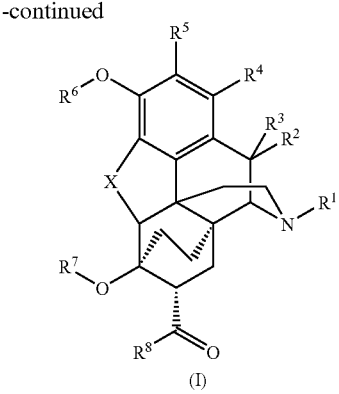

wherein:
  $R^1$, $R^8$ $R^9$, and $R^{10}$ are independently selected from the group consisting of hydrocarbyl and substituted hydrocarbyl;
  $R^2$ and $R^3$ are independently selected from the group consisting of hydrogen, hydrocarbyl and substituted hydrocarbyl;
  $R^4$ and $R^5$ are independently selected from the group consisting of hydrogen, hydrocarbyl, substituted hydrocarbyl, halogen, {—}OH, {—}NH$^2$, {—}SH, {—}SR$^{10}$, and {—}OR$^{10}$;
  $R^6$ and $R^7$ are independently selected from the group consisting of hydrogen, a protecting group, hydrocarbyl, and substituted hydrocarbyl;
  X is oxygen; and
  $X^1$ is a halogen atom;

(b) quenching the reaction product of step (a);
(c) filtering the quenched reaction product of step (b) to form a filtrate comprising an amount of the compound of Formula (I) and an amount of the compound of Formula (II); and
(d) recycling by combining the filtrate of step (c) with the reaction mixture of step (a) and repeating steps (b) and (c).

2. The process of claim 1, wherein $R^1$, $R^6$, $R^7$, and $R^8$ are alkyl or substituted alkyl; and $R^9$ is selected from the group consisting of alkyl, substituted alkyl, aryl, and substituted aryl.

3. The process of claim 2, wherein $R^2$, $R^3$, $R^4$, and $R^6$ are hydrogen.

4. The process of claim 1, wherein $R^9$ is an alkyl or substituted alkyl, and $X^1$ is chloride or bromide.

5. The process of claim 1, wherein step (d) is repeated up to four times.

6. The process of claim 1, wherein the molar ratio of the compound of Formula (I) to $R^9MgX^1$ is from about 1:1 to about 1:5; step (a) is conducted at a temperature of from about 15° C. to about 100° C. and in the presence of a solvent system comprising an aprotic solvent; the reaction of step (b) is cooled to a temperature of less than about 20° C.; and step (d) is repeated up to four times.

7. The process of claim 6, wherein $R^9$ is an alkyl or substituted alkyl; $X^1$ is chloride or bromide; and the solvent system comprises toluene and tetrahydrofuran.

8. The process of claim 6, wherein an amount of the compound of Formula (II) crystallizes in step (b) as the reaction mixture is cooled.

9. The process of claim 1, wherein repeating step (d) four times increases the yield of the compound of Formula (II) by at least 20% compared to when no recycling step (d) is performed.

10. The process of claim 1, wherein the optical activity of the compound of Formula (I) or (II) is selected from the group consisting of (+), (−), and combinations thereof; the configuration of each of C5 and C6 is R; and the configuration of C7, C9, C13, and C14, respectively, is selected from the group consisting of RRSS, RSRR, SRSS, and SSRR, provided that the C15 and the C16 carbons are both either on the alpha face or the beta face of the molecule.

11. A process for the preparation of a compound of Formula (IIa), the process comprising:
(a) forming a reaction mixture that comprises a compound of Formula (Ia) and tertiary-butylMgX$^1$ such that a reaction occurs to yield a reaction product that comprises the compound of Formula (IIa) and an amount of the compound of comprising Formula (Ia) that is unreacted according to the following reaction scheme:

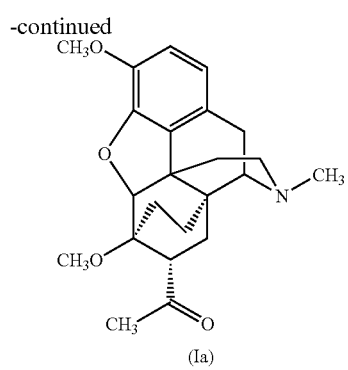

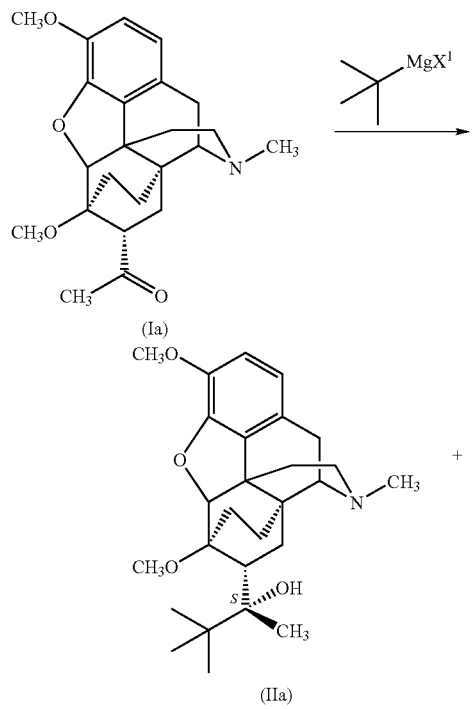

wherein:
$X^1$ is a halogen atom;
(b) quenching the reaction product of step (a);
(c) filtering the quenched reaction product of step (b) to form a filtrate comprising an amount of the compound of Formula (Ia) and an amount of the compound of Formula (IIa); and
(d) recycling by combining the filtrate of step (c) with the reaction mixture of step (a) and repeating steps (b) and (c).

12. The process of claim 11, wherein step (d) is repeated up to four times.

13. The process of claim 11, wherein the molar ratio of the compound of Formula (Ia) to tertiary-butylMgX$^1$ is from about 1:1 to about 1:5; step (a) is conducted at a temperature of from about 15° C. to about 100° C. and in the presence of a solvent system comprising an aprotic solvent; the reaction of step (b) is cooled to a temperature of less than 20° C.; and step (d) is repeated up to four times.

14. The process of claim 13, wherein $X^1$ is chloride or bromide, and the solvent system comprises toluene and tetrahydrofuran.

15. The process of claim 11, wherein an amount of the compound of Formula (IIa) crystallizes in step (b) as the reaction product is cooled.

16. The process of claim 15, wherein the crystallization temperature is from about 15° C. to about 60° C. the first time step (b) is performed.

17. The process of claim 15, wherein the crystallization temperature is from about 25° C. to about 55° C. the fourth time step (b) is performed.

18. The process of claim 11, wherein the yield of the compound of Formula (IIa) is greater than about 70%, based on the amount of the compound of Formula (Ia) mixed with $R^9MgX^1$ in step (a).

19. The process of claim 11, wherein repeating step (d) four times increases the yield of the compound of Formula (IIa) by at least 20% compared to when no recycling step (d) is performed.

20. The process of claim 11, wherein the optical activity of the compound of Formula (Ia) or (IIa) is selected from the group consisting of (+), (−), the configuration of each of C5 and C6 is R; and the configuration of C7, C9, C13, and C14, respectively, is selected from the group consisting of RRSS, RSRR, SRSS, and SSRR, provided that the C15 and the C16 carbons are both either on the alpha face or the beta face of the molecule.

* * * * *